US00PP11146P

United States Patent [19]

Kordes

[11] Patent Number: Plant 11,146

[45] Date of Patent: Dec. 7, 1999

[54] MINIATURE ROSE PLANT NAMED 'KORBRITTA'

[75] Inventor: Wilhelm Kordes, Sparrieshoop, Germany

[73] Assignee: Bear Creek Gardens, Inc., Medford, Oreg.

[21] Appl. No.: 09/045,196

[22] Filed: Mar. 20, 1998

[51] Int. Cl.[6] ..... A01H 5/00

[52] U.S. Cl. ..... Plt./125

[58] Field of Search ..... Plt./118, 119, 125, Plt./126

*Primary Examiner*—Howard J. Locker

*Attorney, Agent, or Firm*—Klarquist Sparkman Campbell Leigh & Whinston, L.L.P.

[57] ABSTRACT

Rose plant of miniature class having a compact, well branched, uniform growth habit; an ability to grow rapidly and flower quickly when grown in a pot from single node softwood cutting; and novel, long lasting, warm, pleasing, amber yellow flower.

1 Drawing Sheet

The present invention relates to a new and distinct variety of rose plant of the miniature class which was originated by me by crossing an unnamed seedling, the parentage of which is 'Korhitom'×'Golden Meillandina'×unnamed seedling, with 'KORdaba' (U.S. Plant Pat. No. 9,116).

The primary objective of this breeding was to produce a new rose variety having a compact growth habit, ability to grow rapidly and flower quickly from softwood cuttings, ability to be grown and flower in pots, to have abundant flowers, to have long lasting flower color and to have good shelf life. The objective was substantially achieved, along with other desirable improvements, as evidenced by the following unique combination of characteristics that are outstanding in the new variety and that distinguish it from its parents, as well as from all other varieties of which I am aware:

1. Compact, well branched growth habit;
2. Rapid, uniform growth from single node softwood cuttings;
3. Grows rapidly and flowers quickly when grown in 10 cm. pots;
4. Long shelf life;
5. Novel, long lasting, warm, pleasing, amber yellow flower color.

'KORbritta' can also be grown as an attractive miniature garden rose.

Asexual reproduction of this new variety by cuttings, as performed at Somis and Wasco, Calif. and Sparrieshoop, Germany, shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling, the parentage of which is 'Korhitom'×'Golden Meillandina'× unnamed seedling.

*Pollen parent.*—'KORdaba' (U.S. Plant Pat. No. 9,116).

Classification:

*Botanical.*—*Rosa hybrida.*

*Commercial.*—Miniature.

FLOWER

Observations made from specimens grown in a greenhouse environment at Somis, Calif. and Sparrieshoop, Germany.

Blooming habit: Continuous.

Bud:

*Size.*—¾" long when the petals start to unfurl.

*Form.*—Long, pointed ovoid.

*Color.*—When sepals first divide, bud color is Yellow Orange Group 21A. When half blown, the upper sides of the petals are Yellow Orange Group 21B, the lower sides of the petals are Yellow Orange Group 21B.

*Sepals.*—Color: Green Group 137D. Surface texture: Covered in fine hairs. There are three normally appendaged sepals. There are two unappendaged sepals with hairy edges.

*Receptacle.*—Color: Yellow Green Group 146B. Shape: Funnel. Size: Medium (¼×3/16"). Surface: Smooth.

*Peduncle.*—Length: Short (1¾"). Surface: Prickly. Color: Medium green. Strength: Stiff, erect.

Bloom:

*Size.*—Small. Average open size is 2–2¼".

*Borne.*—Singly and several together in clusters of 3 to 5 having flat shape.

*Stems.*—Short (6–7"), strong.

*Form.*—When first open: High centered. Permanence: All petals curl; quill fashion.

*Petalage.*—Number of petals under normal conditions: 20–25.

*Color.*—The upper sides of the petals are Yellow Orange Group 21B. The reverse sides of the petals are Yellow Orange Group 21B. The base of each petal has a very small area with a slightly greenish cast at the point of attachment. The major color on the upper sides is Yellow Orange Group 21B.

*Variegations.*—None.

*Discoloration.*—At the end of the first day: No change. At the end of the third day: No change. Color is stable through day 10 on the plant when petals start to fade to Yellow Orange Group 21C and D.

*Fragrance.*—Slight.

Petals:

*Texture.*—Thick.

*Shape.*—Deltoid.

*Form.*—Tips slightly recurved; edges slightly quilled.

*Arrangement.*—Imbricated. Petaloids in the center are few.

*Persistence.*—Petals drop off cleanly before drying.

*Lastingness.*—On the plant: Very long (10–12 days). As a cut flower: Very long (12–14 days).

Reproductive parts:

*Anthers.*—Size: Medium. Quantity: Many. Color: Yellow. Arrangement: Regular around styles.

*Filaments.*—Color: Yellow.

*Pollen.*—Color: Gold yellow.

*Styles.*—Color: Yellow.

*Stigmas:*—Greenish white.

Plant:

*Form.*—Bush.

*Growth.*—Vigorous; dwarf; upright; branching: Height of mature plant grown in the garden is twenty-four to thirty inches, width is eighteen to twenty inches.

Foliage: Number of leaflets on normal mid-stem leaves: Five or seven, or rarely nine.

*Size.*—Small (3 to 3½"×1½to 2").

*Quantity.*—Abundant.

*Color.*—New foliage: Upper and lower surface: Greyed-Orange Group 176A quickly turns to Yellow Green Group 146A on upper surface and Yellow Green Group 146C on lower surface. Old foliage: Upper surface: Green Group 139A. Lower surface: Green Group 138B.

Leaflets:

*Shape.*—Pointed oval.

*Texture.*—Upper side: Leathery, glossy.

*Edge.*—Serrated.

*Serration.*—Single, small.

*Petiole rachis.*—Color: Reddish.

*Petiole underside.*—Smooth.

*Stiples.*—Medium (⅜"–½"); serrated, bearded.

*Disease resistance.*—Resistant to mildew under normal growing conditions at Somis, Calif. and Sparrieshoop, Germany.

Wood:

*New wood.*—Color: Light Green. Bark: Smooth.

*Old wood.*—Color: Green. Bark: Smooth.

Prickles:

*Quantity.*—On main canes from base: Ordinary. On laterals from main canes: Ordinary.

*Form.*—Medium; hooked slightly downward.

*Color when young.*—Red.

Small prickles:

*Quantity.*—On main stalks: None. On laterals: None.

I claim:

1. A new and distinct variety of rose plant of the miniature rose class, substantially as herein shown and described, characterized particularly by its compact, well branched, uniform growth habit; ability to grow rapidly and flower quickly when grown in a pot from single node softwood cutting; and its novel, long lasting, warm, pleasing, amber yellow flower.

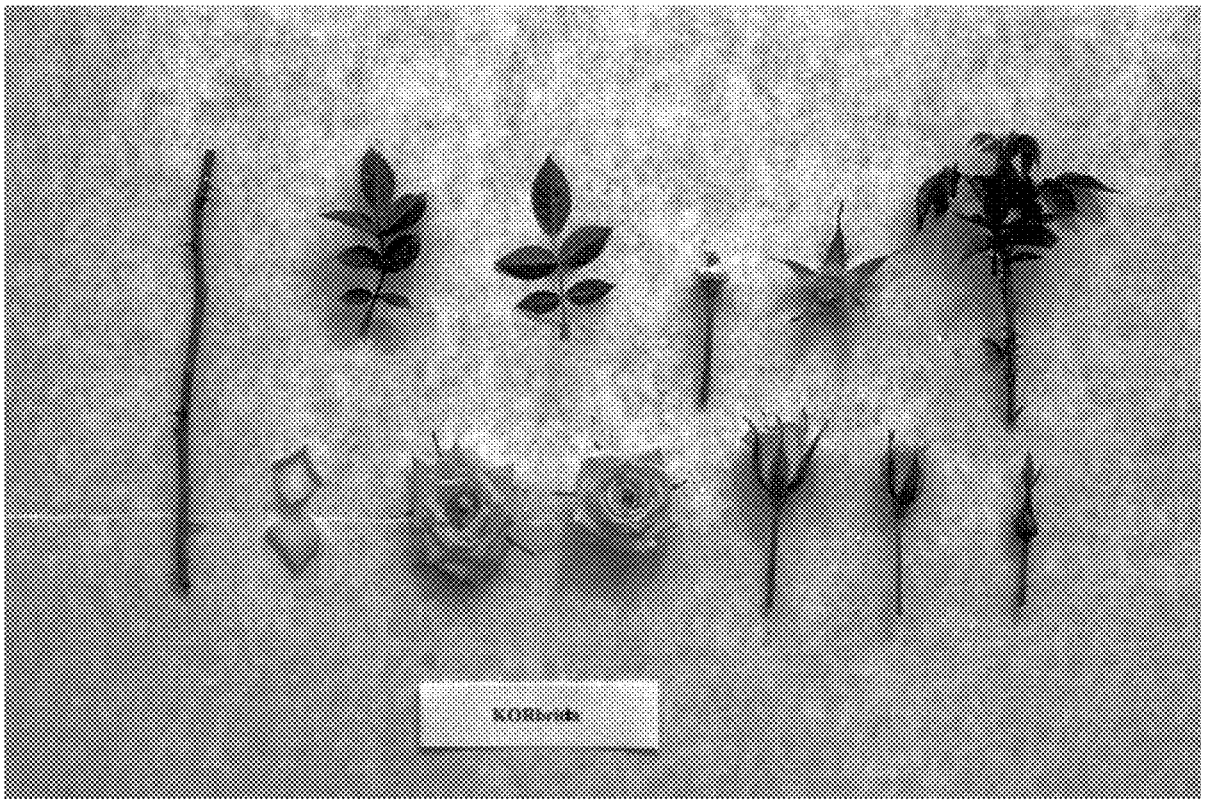

* * * * *